US008137935B2

(12) United States Patent
Caroff

(10) Patent No.: US 8,137,935 B2
(45) Date of Patent: Mar. 20, 2012

(54) METHOD FOR ISOLATING ENDOTOXINS

(75) Inventor: Martine Caroff, Velizy (FR)

(73) Assignee: Universite Paris SUD XI, Orsay (FR)

( * ) Notice: Subject to any disclaimer, the term of this patent is extended or adjusted under 35 U.S.C. 154(b) by 1214 days.

(21) Appl. No.: 10/542,090

(22) PCT Filed: Dec. 8, 2003

(86) PCT No.: PCT/FR03/03617
§ 371 (c)(1),
(2), (4) Date: Apr. 20, 2006

(87) PCT Pub. No.: WO2004/062690
PCT Pub. Date: Jul. 29, 2004

(65) Prior Publication Data
US 2007/0020292 A1    Jan. 25, 2007

(30) Foreign Application Priority Data
Dec. 9, 2002   (FR) ..................... 02 15555

(51) Int. Cl.
*A61K 39/02* (2006.01)
(52) U.S. Cl. .............. 435/72; 514/2.1; 424/234.1
(58) Field of Classification Search ......... None
See application file for complete search history.

(56) References Cited

U.S. PATENT DOCUMENTS

| | | | | |
|---|---|---|---|---|
| 3,328,253 A * | 6/1967 | Watanabe | .................. 424/261.1 |
| 4,242,270 A * | 12/1980 | Ayme et al. | ........................ 554/1 |
| 4,663,306 A * | 5/1987 | Cantrell | ..................... 424/282.1 |
| 4,831,126 A * | 5/1989 | Bundle et al. | ................... 536/53 |
| 5,169,535 A * | 12/1992 | Adachi et al. | ................ 210/669 |
| 5,391,715 A * | 2/1995 | Capiau et al. | ................ 530/396 |
| 5,403,917 A * | 4/1995 | Boos et al. | .................... 530/351 |
| 5,824,310 A * | 10/1998 | Golding | .................... 424/193.1 |
| 6,106,723 A * | 8/2000 | Grandics et al. | ............. 210/651 |
| 6,461,517 B1 * | 10/2002 | Miwa et al. | ................... 210/690 |
| 6,617,443 B2 * | 9/2003 | Hendriks et al. | ........... 536/25.41 |
| 6,773,599 B1 * | 8/2004 | Lowe et al. | ................... 210/635 |
| 6,774,102 B1 * | 8/2004 | Bell et al. | ......................... 514/2 |
| 2003/0031684 A1 * | 2/2003 | Myers et al. | ................ 424/236.1 |
| 2007/0213258 A1 * | 9/2007 | Nakayama et al. | ............... 514/8 |

FOREIGN PATENT DOCUMENTS

EP    0 976 402    2/2000

OTHER PUBLICATIONS

Therisod, Helene et al, Analytical Chemistry, 2001, vol. 73, pp. 3804-3807, Directe microextraction and analysis of rough type lipopolysaccharides by Combined thin-layer chromatography and MALDI Mass Spectrometry.*
Therisod et al, reference of record.*
Caroff, MG et al, reference of record.*

(Continued)

*Primary Examiner* — Albert Navarro
*Assistant Examiner* — Ginny Portner
(74) *Attorney, Agent, or Firm* — Oblon, Spivak, McClelland, Maier & Neustadt, L.L.P.

(57) ABSTRACT

The invention concerns a novel method for extracting endotoxins from bacteria, and the use of said method for preparing compositions comprising endotoxins or derivatives thereof designed for human or animal use (scientific, medical usage).

57 Claims, 1 Drawing Sheet

Comparative thin layer chromatography of
the endotoxins isolated by means of the former
and the new method

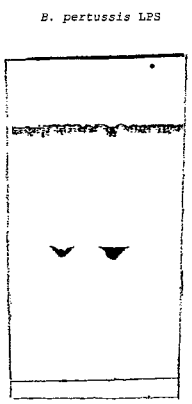

B. pertussis LPS phenol/water   isobutyric

OTHER PUBLICATIONS

Le Dur et al, European Journal of Biochemistry, vol. 84, pp. 579-589, 1978, A Novel type of Endotoxin Structure present in *Bordetella pertussis*.*

Caroff, Martine G. L. et al.: "Several Uses for Isobutyric Acid-Ammonium Hydroxide Solvent in Endotoxin Analysis", Applied and Environmental Microbiology, vol. 56, No. 6, pp. 1957-1959, Jun. 1990. XP008024672.

Therison, Helene et al.: "Direct Microextraction and Analysis of Rough-Type Lipopolysaccharides by Combined Thin-Layer Chromatography and MALDI Mass Spectrometry", Analytical Chemistry, vol. 73, No. 16, pp. 3804-3807, Aug. 15, 2001. XP-002262340.

Ridley, Brent L. et al.: "The type and yield of lipopolysaccharide from symbiotically deficient *Rhizobium* lipopolysaccharide mutants vary depending on the extration method", Glycobiology, vol. 10, No. 10, pp. 1013-1023, Oct. 2000. XP008024739.

Valverde, Claudio et al.: "Rapid Preparation of Affinity-Purified Lipo-polysaccharide Samples for Electrophoretic Analysis" BioTechniques, vol. 22, No. 2, pp. 230, 232, 234, 236, 1997. XP-001160910.

Di Fabio, J.L. et al.: "Characterization of the common antigenic lipopolysaccharide O-chains produced by *Bordetella bronchiseptica* and *Bordetella parapertussis*", FEMS Microbiology Letters, vol. 97, No. 3, pp. 275-281, 1992. XP008024673.

* cited by examiner

Comparative thin layer chromatography of
the endotoxins isolated by means of the former
and the new method

*B. pertussis* LPS phenol/water    isobutyric

FIGURE 1

METHOD FOR ISOLATING ENDOTOXINS

The invention relates to a novel method for extracting endotoxins from bacteria, in particular Gram-negative bacteria, and also to the use of this method for preparing compositions comprising endotoxins or derivatives thereof, and intended for human or animal use (scientific use, medical use, etc.).

Endotoxins are powerful stimulators of the immune system (induction of interleukins, TNF, NO, etc.). They are the main constituents of the outer membranes of Gram-negative bacteria. Endotoxins are mixtures of lipopolysaccharides or LPSs.

Among bacterial colonies, two categories are mainly distinguished: those referred to as type S, for "smooth", relating to the smooth appearance of the colony; and those referred to as type R, for "rough", this term recalling the rough morphology of the colony. A third category, referred to as SR for "semi-rough", also exists.

The structure of LPSs constituting bacterial endotoxins is different depending on whether the bacteria are R-type or S-type bacteria. LPSs consist of a lipid domain referred to as lipid A and of a "core" poly-saccharide chain attached to the lipid A.

S-type LPSs also contain an "O-type" antigenic chain. R-type LPSs do not contain this O-type antigenic chain. SR-type LPSs contain a single unit of the O-type anti-genic chain.

The present invention relates more particularly to the isolation of endotoxins from an R-type bacterial culture, and optionally an SR-type bacterial culture. However, it may also be applied to S-type bacterial cultures.

In the methods of the prior art, bacterial endotoxins were isolated by extraction using a mixture of solvents that could be a mixture of phenol and water or a mixture of chloroform, petroleum ether and phenol. These methods have the serious drawback of using toxic solvents and therefore of causing health risks for the individuals who have to handle them. A method of extraction with trichloroacetic acid also exists; however, this method results in too much contamination to be considered satisfactory.

In addition, residues of toxic solvents in the bacterial endotoxin extracts made them unfit for human or animal administration and also for use in scientific experiments. Finally, the elimination of these residues of toxic solvents constituted a difficult and expensive step in the method of the prior art.

The document M. Caroff and D. Karibian. "Several uses for Isobutyric Acid-Ammonium Hydroxide solvent in endotoxin analysis" Applied and Env. *Microbiol.* 56: 1957-1959 (1990), describes the use of the mixture of solvents isobutyric acid/$NH_4OH$ (molar) (5:3) for determining the purity of bacterial endotoxins by chromatography and also for differentiating bacterial endotoxins derived from various strains.

That document also describes a method for purifying natural endotoxins from endotoxins isolated according to one of the conventional methods of extraction with phenol in a first step. In the second step of this method, the endotoxins are purified by extraction using the mixture of solvents isobutyric acid/$NH_4OH$ (molar) (5:3).

The extract is centrifuged and the supernatant is recovered. The solvents are evaporated off. The endotoxin is recovered by trituration with ethanol.

On reading that document, those skilled in the art understand that phenol extraction constitutes the indispensable first step of any method for isolating bacterial endotoxins.

The document H. Thérisod, V. Labas and M. Caroff. "Direct microextraction and analysis of rough-type lipopolysaccharides by combined thin-layer chromatography and MALDI mass spectrometry". *Anal. Chem.* 73: 3804-3807 (2001), describes a method for isolating bacterial endotoxins directly from bacteria by chromatography on a silica plate, the eluent used being the mixture of solvents isobutyric acid/$NH_4OH$ (5:3).

However, silica plate chromatography and solvent extraction are two quite distinct separating techniques and no correlation exists between the results obtained by means of these two techniques.

Thus, it is with surprise that the applicant has discovered a novel method for isolating bacterial endotoxins (or lipopolysaccharides) directly from bacteria.

The method according to the invention is characterized in that:
  the starting product is a group of bacterial cells or, optionally, a culture supernatant;
  in a first step, the bacterial cells, or the culture supernatant, are (is) suspended in a mixture of solvents consisting of:
    10 to 90%, preferably 30 to 70%, of a solvent chosen from: linear or branched aliphatic acids containing from 3 to 6 carbon atoms
    90 to 10%, preferably 70 to 30%, of a basic aqueous solution of an aliphatic amine containing from 0 to 12 carbon atoms
    and the entire mixture is stirred, to give a solution in which particles are in suspension,
  in a second step, the particles in suspension are separated from the solution:
    either by filtration of the composition,
    or by centrifugation and recovery of the supernatant,
    or by centrifugation followed by filtration of the supernatant;
  in a third step, the solvents are eliminated from the supernatant or from the filtrate by any means known to those skilled in the art, such as in particular: dialysis, filtration/washing, precipitation of the LPSs, for example by adding ethanol.

The method according to the present invention has many advantages compared with the methods of the prior art. It is rapid: the endotoxins are extracted in 12 to 24 hours or less, whereas in the phenol extraction methods, the extraction step itself lasted at least a week.

This method does not use silica, it is simpler to carry out, in particular on an industrial scale.

This method does not use toxic solvents, it is not therefore dangerous for the handlers who implement it.

It is very selective.

The yields are 2 to 10 times higher than those obtained by means of the methods of the prior art, for the bacteria already tested.

The usual enzymatic treatments with DNAse, RNAse and protease, conventionally used to eliminate DNA and RNA contaminants, and residual peptides and proteins, are not generally necessary.

In addition, the absence of toxic solvents, the rapidity and the good yields of the method of the invention make it possible to envision its extrapolation to an industrial scale.

Finally, many recent articles demonstrate that certain LPSs currently on the market, and obtained by extraction in a phenol/water system, carry contaminants that mean they cannot be used in scientific experiments. The LPSs obtained by means of the method of the invention have the advantage of not carrying contaminants.

Among the aliphatic acids that may be used in the present invention, a branched acid is preferably chosen. Aliphatic acids containing 4 carbon atoms, such as butyric acid and isobutyric acid, are preferred. The aliphatic acid preferably used in the present invention is isobutyric acid.

Among the aliphatic amines that may be used in the present invention, mention may in particular be made of: aqueous ammonia, diisopropylethylamine and tri-ethylamine. Aqueous ammonia or triethylamine is preferably chosen. The aliphatic amines are used in an aqueous solution having a concentration ranging from 5 to 20%, preferably having a concentration in the region of 10%.

The composition resulting from the first step is a heterogeneous composition comprising, firstly, particles of cell debris in suspension and, secondly, the bacterial endotoxins in solution in the mixture of solvents.

The elimination of the particles of cell debris by filtration and/or centrifugation makes it possible to isolate the endotoxins.

If it is desired to purify the endotoxins with respect to any possible contaminating residues, the composition derived from the third step of the method of the invention (dialysate or precipitated LPS that is taken up in water) can be extracted with methanol or with a mixture of chloroform and methanol, so as to eliminate in particular contaminating phospholipid or lipoprotein residues.

Depending on the desired use for which they are intended, the endotoxins, derived from the method of the invention, can be conserved in an aqueous solution or can be lyophilized in order to store them in powdered form, the latter solution having the advantage of facilitating the handling and the dosing thereof.

The bacterial cells used as starting product are preferably Gram-negative cells. However, it is also possible to envision using the method according to the invention for purifying other phosphoglycans or lipoglycans isolated from other bacterial types, in particular for the purposes of vaccines.

Cells preferably used in the method of the invention are: *Bordetella pertussis, Escherichia coli, Bordetella parapertussis, Salmonella, Shigella, Pseudomonas, Neisseria* and *Haemophilus*.

The bacterial cells are generally obtained by centrifugation of a culture medium and recovery of the bacterial pellet. However, during this centrifugation process, it is possible to recover a supernatant that may be rich in lipopolysaccharides and can constitute a starting product for application of the method of the invention.

The mixtures of solvents preferably used are: isobutyric acid and either aqueous ammonia in a molar aqueous solution or triethylamine in a 10% aqueous solution (percentage by volume).

A mixture of isobutyric acid and of aqueous ammonia in a molar aqueous solution, in a 5/3 ratio by volume, or a mixture of isobutyric acid and of triethylamine in a 10% aqueous solution, in a 5/3 ratio by volume, is preferably used.

Advantageously, the stirring corresponding to the first step of the method of the invention lasts from 5 to 15 minutes. Even more advantageously, it lasts from 10 to 15 minutes.

The filtration is preferably carried out on a support having a porosity ranging from 0.1 to 2 µm.

Even more preferably, it ranges from 0.2 to 0.45 µm.

When the mixture derived from the first step is centrifuged, this centrifugation is preferably carried out under the following conditions: 1500 to 3000 g, for 10 to 20 minutes at ambient temperature, preferably 2000 g for approximately 15 minutes.

The method according to the invention makes it possible to obtain the endotoxins rapidly, with very good yields, and substantially free of biological contaminants or of solvents.

All these properties make it possible to envision applications which, up until now, could be implemented only with difficulty.

A particular case is the preparation of compositions intended for human or animal administration. Because of the toxicity of the solvents used in the prior art and the purification difficulties that they caused, such applications could not be envisioned. Because of the method of the invention, it is now possible to prepare compositions, in particular therapeutic compositions, that can be administered to humans or to animals (with the proviso that the molecules themselves are not toxic) by any routes: oral, injection, application to the skin or the mucous membranes.

In particular, it is possible to prepare, by means of this method, vaccine compositions comprising endotoxins, or endotoxin derivatives, on an industrial scale.

Among the endotoxin derivatives, mention may in particular be made of detoxified endotoxins, endotoxin fragments, endotoxins conjugated with other molecules, in particular with proteins.

The use of endotoxins for preparing vaccine compositions is mentioned in particular in EP-976402.

A subject of the invention is also therefore a method for preparing a composition comprising one or more endotoxins or endotoxin derivatives, such as in particular endotoxin fragments or detoxified endotoxins, intended for human or animal administration, characterized in that it comprises a step consisting in isolating the endotoxins as described above. In a second step, the isolated endotoxins are incorporated into a suitable vehicle, in particular a pharmaceutically acceptable vehicle. They may also be packaged directly for the purpose of an extemporaneous preparation of the composition intended for human or animal administration.

The endotoxins may also be directly sold for scientific use.

EXPERIMENTAL SECTION

Cells are placed in culture according to a method already described by J. L. Di Fabio; M. Caroff; D. Karibian; J. C. Richards and M. B. Perry, *FEMS Microbiol. Lett.* 1992, 76: 275-281.

Those skilled in the art know how to adapt the culture conditions according to the cell type concerned.

One gram of lyophilized cells (or the equivalent of wet bacterial pellet) is suspended in 50 ml of a mixture of isobutyric cid and molar $NH_4OH$ (5:3) and gently stirred by means of magnetic stirring for 5 minutes. The mixture is centrifuged at 2000 g for 15 minutes at ambient temperature. The clarified supernatant, containing the endotoxin, is filtered through glass fiber paper (Whatman GF/D), diluted with three volumes of distilled water and dialyzed. A second extraction of the pellet may be carried out if necessary. The retentate from the dialysis is filtered through glass fiber paper under the same conditions as previously, and then lyophilized, and it is extracted with a mixture of chloroform and methanol (1:2) in order to remove the possible phospholipid contaminants. The residue from the extraction is then lyophilized. The two filtration steps can be carried out over sintered glass (16-40 µm) covered with the glass fiber paper, and a partial vacuum can be applied in order to accelerate the process, with the proviso that the quality of the filtrate is controlled on TLC.

The yield is from 2 to 10% according to the bacteria.

The extraction is carried out in 24 hours. This period of time can be further reduced to a few hours by means of filtration dialysis methods, applicable on an industrial scale.

These trials were carried out successfully on bacteria of the *Bordetella* genus (*B. pertussis*, the agent for whooping cough, and other bacteria of the same bacterial genus that are responsible for respiratory infections). This method was also tested on cells of *Escherichia coli* K 12 and of *Neisseria meningitidis*.

When the bacteria comprise capsid polysaccharides in a large amount, it may be advantageous to eliminate them by washing the cells prior to performing the extraction.

A comparison of the endotoxins obtained from *Bordetella pertussis* by means of the present method (marked isobutyric) and the phenol-water method is shown in FIG. 1, which represents comparative thin layer chromatography of the endotoxins isolated by means of these two methods. A comparison by SDS-PAGE gel, TLC and mass spectrometry made it possible to verify the effectiveness of the method and the integrity of the endotoxins.

The invention claimed is:

1. A method for isolating one or more endotoxins, comprising:
    suspending a group of bacterial cells or a culture supernatant, wherein the bacterial cells or the culture supernatant contain the endotoxins, in a mixture of solvents containing:
        10 to 90% of a solvent chosen from: linear or branched aliphatic acids containing from 3 to 6 carbon atoms, and
        90 to 10% of a basic aqueous solution of an aliphatic amine containing from 0 to 12 carbon atoms;
    stirring the suspended bacterial cells or a culture supernatant to produce a solution of bacterial endotoxins in the mixture of solvents containing suspended particles of cell debris; and
    separating the particles from the solution by (1) filtration, (2) centrifugation and recover of the supernatant or (3) centrifugation followed by filtration of the supernatant, to produce the isolated endotoxins,
    wherein the endotoxins are not obtained in combination with silica.

2. The method of claim 1, wherein the bacterial cells are Gram-negative bacteria.

3. The method of claim 1, wherein the bacterial cells are R-type or SR-type Gram-negative bacteria.

4. The method of claim 1, wherein the bacterial cells are *Bordetella pertussis*.

5. The method of claim 1, wherein the cells are *Escherichia coli, Bordetella parapertussis, Salmonella, Shigella, Pseudomonas, Neisseria* or *Haemophilus*.

6. The method of claim 1, wherein the solvents are eliminated from the supernatant or from the filtrate containing endotoxins by means of a method chosen from: dialysis, filtration/washing, or precipitation.

7. The method of claim 6, further comprising extracting the endotoxins with a mixture of chloroform and methanol.

8. The method of claim 1, wherein the mixture of solvents contains:
    30 to 70% of a solvent chosen from linear or branched aliphatic acids containing from 3 to 6 carbon atoms,
    70 to 30% of a basic aqueous solution of an aliphatic amine containing from 0 to 12 carbon atoms.

9. The method of claim 1, wherein the mixture of solvents is isobutyric acid and triethylamine in a 10% aqueous solution, in a 5/3 ratio by volume.

10. The method of claim 1, wherein the mixture of solvents is a mixture of isobutyric acid and of aqueous ammonia in a molar aqueous solution, in a 5/3 ratio by volume.

11. The method of claim 1, wherein the suspending lasts from 5 to 15 minutes.

12. The method of claim 1, wherein the aliphatic amine is ammonia.

13. The method of claim 1, wherein the mixture of solvents consists of:
    10 to 90% of the solvent chosen from: linear or branched aliphatic acids containing from 3 to 6 carbon atoms, and
    90 to 10% of the basic aqueous solution of an aliphatic amine containing from 0 to 12 carbon atoms.

14. A method for isolating one or more endotoxins, comprising:
    suspending 1 gram or more of a group of bacterial cells or a culture supernatant containing 1 gram or more of bacterial cells, wherein the bacterial cells or the culture supernatant contain the endotoxins, in a mixture of solvents containing:
        10 to 90% of a solvent chosen from: linear or branched aliphatic acids containing from 3 to 6 carbon atoms, and
        90 to 10% of a basic aqueous solution of an aliphatic amine containing from 0 to 12 carbon atoms;
    stirring the suspended bacterial cells or a culture supernatant to produce a solution of bacterial endotoxins in the mixture of solvents containing suspended particles of cell debris;
    separating the particles from the solution by (1) filtration, (2) centrifugation followed by recovery of the resulting supernatant or (3) centrifugation followed by filtration of the resulting supernatant; and
    eliminating solvents from the filtrate or supernatant containing endotoxins.

15. The method of claim 14, wherein the bacterial cells are Gram-negative bacteria.

16. The method of claim 14, wherein the bacterial cells are R-type or SR-type Gram-negative bacteria.

17. The method of claim 14, wherein the bacterial cells are *Bordetella pertussis*.

18. The method of claim 14, wherein the cells are *Escherichia coli, Bordetella parapertussis, Salmonella, Shigella, Pseudomonas, Neisseria* or *Haemophilus*.

19. The method of claim 14, wherein the solvents are eliminated from the supernatant or from the filtrate by dialysis, filtration/washing, or precipitation.

20. The method of claim 14, further comprising extracting the endotoxins with a mixture of chloroform and methanol.

21. The method of claim 14, wherein the mixture of solvents contains:
    30 to 70% of a solvent chosen from linear or branched aliphatic acids containing from 3 to 6 carbon atoms,
    70 to 30% of a basic aqueous solution of an aliphatic amine containing from 0 to 12 carbon atoms.

22. The method of claim 14, wherein the mixture of solvents is isobutyric acid and triethylamine in a 10% aqueous solution, in a 5/3 ratio by volume.

23. The method of claim 14, wherein the mixture of solvents is a mixture of isobutyric acid and of aqueous ammonia in a molar aqueous solution, in a 5/3 ratio by volume.

24. The method of claim 14, wherein the suspending lasts from 5 to 15 minutes.

25. The method of claim 14, wherein the filtration is carried out on a support having a porosity ranging from 0.1 to 2 μm.

26. The method of claim 14, wherein the centrifugation is carried out under the following conditions: 1500 to 3000 g, for 10 to 20 minutes at ambient temperature.

27. The method of claim 14, wherein the aliphatic amine is ammonia.

28. The method of claim 14, wherein the mixture of solvents consists of:
   10 to 90% of the solvent chosen from: linear or branched aliphatic acids containing from 3 to 6 carbon atoms, and
   90 to 10% of the basic aqueous solution of an aliphatic amine containing from 0 to 12 carbon atoms.

29. A method for isolating one or more endotoxins, comprising:
   suspending a group of bacterial cells or a culture supernatant, wherein the bacterial cells or the culture supernatant contain the endotoxins, in a mixture of solvents containing:
      10 to 90% of a solvent chosen from: linear or branched aliphatic acids containing from 3 to 6 carbon atoms, and
      90 to 10% of a basic aqueous solution of an aliphatic amine containing from 0 to 12 carbon atoms;
   stirring the suspended bacterial cells or a culture supernatant to produce a solution of baterial endotoxins in the mixture of solvents containing suspended particles of cell debris;
   separating the particles from the solution by (1) filtration, (2) centrifugation followed by recovery of the resulting supernatant or (3) centrifugation followed by filtration of the resulting supernatant; and
   eliminating solvents from the filtrate or supernatant containing endotoxins,
   wherein the method is conducted on an industrial scale.

30. The method of claim 29, wherein the bacterial cells are Gram-negative bacteria.

31. The method of claim 29, wherein the bacterial cells are R-type or SR-type Gram-negative bacteria.

32. The method of claim 29, wherein the bacterial cells are *Bordetella pertussis*.

33. The method of claim 29, wherein the cells are *Escherichia coli, Bordetella parapertussis, Salmonella, Shigella, Pseudomonas, Neisseria* or *Haemophilus*.

34. The method of claim 29, wherein the solvents are eliminated from the supernatant or from the filtrate dialysis, filtration/washing, or precipitation.

35. The method of claim 29, further comprising extracting the endotoxins with a mixture of chloroform and methanol.

36. The method of claim 29, wherein the mixture of solvents contains:
   30 to 70% of a solvent chosen from linear or branched aliphatic acids containing from 3 to 6 carbon atoms,
   70 to 30% of a basic aqueous solution of an aliphatic amine containing from 0 to 12 carbon atoms.

37. The method of claim 29, wherein the mixture of solvents is isobutyric acid and triethylamine in a 10% aqueous solution, in a 5/3 ratio by volume.

38. The method of claim 29, wherein the mixture of solvents is a mixture of isobutyric acid and of aqueous ammonia in a molar aqueous solution, in a 5/3 ratio by volume.

39. The method of claim 29, wherein the suspending lasts from 5 to 15 minutes.

40. The method of claim 29, wherein the filtration is carried out on a support having a porosity ranging from 0.1 to 2 μm.

41. The method of claim 29, wherein the centrifugation is carried out under the following conditions: 1500 to 3000 g, for 10 to 20 minutes at ambient temperature.

42. The method of claim 29, wherein the aliphatic amine is ammonia.

43. The method of claim 29, wherein the mixture of solvents consists of:
   10 to 90% of the solvent chosen from: linear or branched aliphatic acids containing from 3 to 6 carbon atoms, and
   90 to 10% of the basic aqueous solution of an aliphatic amine containing from 0 to 12 carbon atoms.

44. A method for isolating one or more endotoxins, comprising:
   suspending a group of bacterial cells or a culture supernatant, wherein the bacterial cells or the culture supernatant contain the endotoxins, in a mixture of solvents containing:
      10 to 90% of a solvent chosen from: linear or branched aliphatic acids containing from 3 to 6 carbon atoms, and
      90 to 10% of a basic aqueous solution of an aliphatic amine containing from 0 to 12 carbon atoms;
   stirring the suspended bacterial cells or a culture supernatant to produce a solution pf bacterial endotoxins in the mixture of solvents containing suspended particles of cell debris;
   separating the particles from the solution by centrifugation and recovery of the resulting supernatant; and
   eliminating solvents from the supernatant containing endotoxins.

45. The method of claim 44, wherein the bacterial cells are Gram-negative bacteria.

46. The method of claim 44, wherein the bacterial cells are R-type or SR-type Gram-negative bacteria.

47. The method of claim 44, wherein the bacterial cells are *Bordetella pertussis*.

48. The method of claim 44, wherein the cells are *Escherichia coli, Bordetella parapertussis, Salmonella, Shigella, Pseudomonas, Neisseria* or *Haemophilus*.

49. The method of claim 44, wherein the solvents are eliminated from the supernatant or from the filtrate by dialysis, filtration/washing, or precipitation.

50. The method of claim 44, further comprising extracting the endotoxins with a mixture of chloroform and methanol.

51. The method of claim 44, wherein the mixture of solvents contains:
   30 to 70% of a solvent chosen from linear or branched aliphatic acids containing from 3 to 6 carbon atoms,
   70 to 30% of a basic aqueous solution of an aliphatic amine containing from 0 to 12 carbon atoms.

52. The method of claim 44, wherein the mixture of solvents is isobutyric acid and triethylamine in a 10% aqueous solution, in a 5/3 ratio by volume.

53. The method of claim 44, wherein the mixture of solvents is a mixture of isobutyric acid and of aqueous ammonia in a molar aqueous solution, in a 5/3 ratio by volume.

54. The method of claim 44, wherein the suspending lasts from 5 to 15 minutes.

55. The method of claim 44, wherein the centrifugation is carried out under the following conditions: 1500 to 3000 g, for 10 to 20 minutes at ambient temperature.

56. The method of claim 44, wherein the aliphatic amine is ammonia.

57. The method of claim 44, wherein the mixture of solvents consists of:
   10 to 90% of the solvent chosen from: linear or branched aliphatic acids containing from 3 to 6 carbon atoms, and
   90 to 10% of the basic aqueous solution of an aliphatic amine containing from 0 to 12 carbon atoms.

* * * * *